(12) United States Patent
Fritz et al.

(10) Patent No.: US 7,808,640 B2
(45) Date of Patent: Oct. 5, 2010

(54) PHOTOACOUSTIC SPECTROSCOPY SYSTEM

(75) Inventors: Bernard E. Fritz, Eagan, MN (US); Matthew S. Marcus, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/182,688

(22) Filed: Jul. 30, 2008

(65) Prior Publication Data

US 2010/0027012 A1    Feb. 4, 2010

(51) Int. Cl.
*G01N 21/00* (2006.01)
(52) U.S. Cl. .................. 356/432; 356/439; 356/931; 356/932
(58) Field of Classification Search .......... 356/432, 356/928, 931, 932, 440, 439, 437
See application file for complete search history.

(56) References Cited

U.S. PATENT DOCUMENTS

| | | | |
|---|---|---|---|
| 4,051,372 A * | 9/1977 | Aine | 250/343 |
| 4,732,480 A | 3/1988 | Fortunato et al. | |
| 5,544,186 A | 8/1996 | Sauer et al. | |
| 5,933,245 A * | 8/1999 | Wood et al. | 356/432 |
| 6,151,112 A | 11/2000 | Atkinson et al. | |
| 6,393,894 B1 | 5/2002 | Bonne et al. | |
| 2007/0146720 A1 | 6/2007 | Cox et al. | |
| 2008/0159341 A1* | 7/2008 | Patel et al. | 356/437 |

FOREIGN PATENT DOCUMENTS

| | | |
|---|---|---|
| KR | 20060087792 | 8/2006 |
| WO | 2006000120 | 1/2006 |

* cited by examiner

*Primary Examiner*—Gregory J Toatley, Jr.
*Assistant Examiner*—Iyabo S Alli
(74) *Attorney, Agent, or Firm*—Crompton Seager & Tufte LLC

(57) ABSTRACT

A system for providing photoacoustic spectroscopy. A light source having a quantum dot filter may provide a band of infrared light which is to be reflected by a lamellar grating to a photoacoustic chamber. The light may be modulated by the grating. The chamber may contain a sample of fluid for which spectral information is sought. A sensor may detect acoustic pressures in the chamber which indicate the spectral information. Signals from the sensor may be processed and displayed. Identification and concentration of certain substances in the fluid may be obtained.

19 Claims, 6 Drawing Sheets

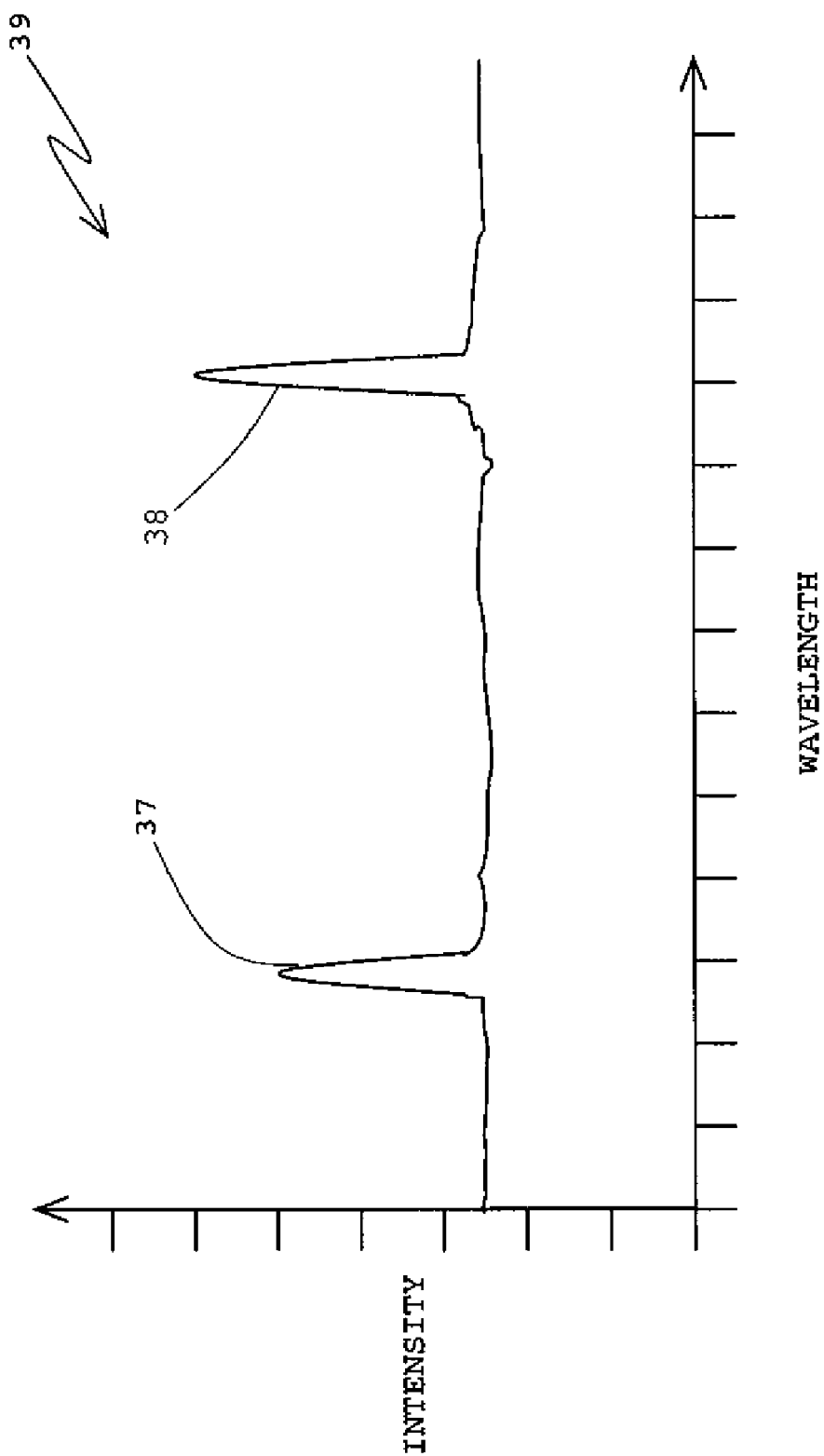

PHOTOACOUSTIC SPECTROSCOPY SYSTEM

BACKGROUND

The invention pertains to spectroscopy and particularly to spectroscopy of fluids. More particularly, the invention pertains to photoacoustic spectroscopy.

SUMMARY

The invention is a photoacoustic spectroscopy system which has a source that provides light to a photoacoustic chamber via a grating. The chamber may contain a sample for which spectral information is sought. A sensor may detect pressures in the chamber.

BRIEF DESCRIPTION OF THE DRAWING

FIG. 6 is a graph of example absorption lines which may occur at an output of the photoacoustic system.

DESCRIPTION

The present invention may provide a photoacoustic measurement with a quantum dot light source, a grating, a photoacoustic chamber or cell, and a sensitive pressure sensor situated at the photoacoustic chamber. Photoacoustic measurement is based on the tendency of molecules in a gas, when exposed to certain wavelengths of radiant energy (e.g., infrared light), to absorb the energy and reach higher levels of molecular vibration and rotation, thereby attaining a higher temperature and pressure within a measurement cell. When the radiant energy striking a gas is amplitude modulated at a known frequency, the resulting fluctuations in energy available for absorption produce corresponding temperature and pressure fluctuations in the gas, which may be measured as an acoustic signal. The amplitude of the acoustic signal is proportional to the intensity of the radiation and the concentration value of the absorbing gas. Such device may be well suited for measuring very small concentration values of gases (i.e., in the parts-per-billion or better range).

Photoacoustic spectroscopy measurements should have a broadband infrared light source in order to measure a broad range of analytes. Typically, this may require the use of a glowbar blackbody light source and a Michaelson interferometer. While such a system may enable the measurement of many different analytes, it is typically complex (i.e., having a large number of components), has a potentially large form factor (i.e., not portable), and can have a large power budget. A fluid may be or contain the analytes. The fluid may be a gas or a liquid.

A U.S. patent application Ser. No. 12/105,241, filed Apr. 17, 2008, U.S. patent application Ser. No. 11/350,541, filed Feb. 9, 2006, and U.S. Pat. No. 6,393,894, issued May 28, 2002, may relate to the present invention. U.S. patent application Ser. No. 12/105,241, filed Apr. 17, 2008, is hereby incorporated by reference. U.S. patent application Ser. No. 11/350,541, filed Feb. 9, 2006, is hereby incorporated by reference. U.S. Pat. No. 6,393,894, issued May 28, 2002, is hereby incorporated by reference.

Figure 1:
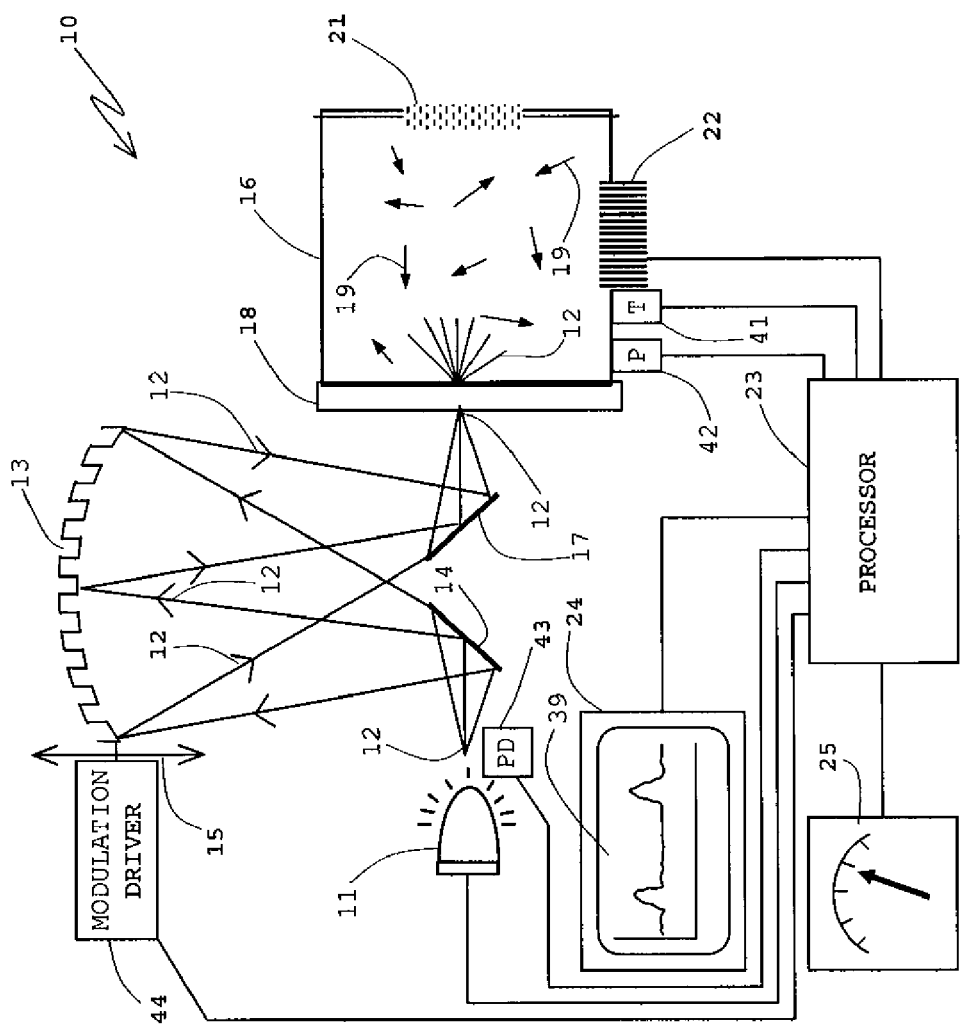
FIG. 1 is a diagram of a photoacoustic system having a grating.

The present invention may be a Fourier transform infrared-photoacoustic spectroscopy (FTIR-PAS) system 10. FIG. 1 is a diagram of the FTIR-PAS system 10. A broadband light source 11 may provide a light 12 to a lamellar grating 13 via a reflective mechanism 14. Light 12 may be modulated by grating 13 as indicated by symbol 15. A modulation driver 44 may be coupled to grating 13 for modulating light 12. Driver 44 may be connected to processor 23. Modulated light 12 may be reflected to a photoacoustic chamber 16 via a reflective mechanism 17 and a window 18 in the chamber. Window 18 may be transparent to the modulated light 12. Window 18 may be silicon in the case of infrared light 12. Photoacoustic chamber 16 may contain a sample 19 of gas such as ambient air or a person's breath brought in through a porous plate 21, i.e., a gas permeable wall, situated over an opening in chamber 16. Porous plate 21 may be replaced with a controllable valve which can seal the sample 19 within the chamber. A pressure sensor 22 may be placed in another opening of chamber 16. An output from the pressure sensor 22 may go to processor 23. The processor may process the signals into a format which reveals the results of system 10 relative to the sample 19 in chamber 16. The results may go to a display 24 for viewing. Display 24 may show the results, for example, in an intensity versus wavelength graph 39. Graph 39 reveals absorption lines 37 and 38 of sample 19, as shown in FIG. 6. The results from processor 23 may also go to an instrument 25 such as a meter for another manner of displaying the results.

System 10 may have several aspects. One is that the system may use a MEMS (Micro-electro-mechanical systems) based lamellar grating 13 to frequency modulate different wavelengths of light from the broadband infrared (IR) source 11. The lamellar grating 13 may reduce the number of components in system 10 compared to other Fourier transform (FT) IR light source systems. Also, the system may use a quantum dot conversion filter to obtain a certain band of light from source 11. The filter may effect a down conversion of a high energy photon to a low energy photon, or possibly multiple low energy photons. Typically, broadband IR light sources may use a blackbody, such as a glowbar or an incandescent light bulb. For instance, quantum dot conversion filters may be used for attaining broadband IR light, result in lower costs and provide higher efficiencies compared to blackbody sources. The conversion filters may also be used for attaining narrow band IR light.

System 10 may use the lamellar grating 13 to frequency modulate different wavelengths of light 12 from source 11. Light 12 from the source 11 may be directed toward a surface of the lamellar grating 13 interferometer.

The light 12 from light source 11 may be produced by a quantum dot conversion filter. In brief, a collection of nanocrystalline quantum dots (i.e., nanocrystals) may be disposed on an optically transparent surface. The surface may be at the output of the light source 11. An excitation light, such as that of a low-cost LED, may optically pump the quantum dot collection. The quantum dots may be judiciously chosen such that the fluorescence response to the optical stimulus results in, for example, a broadband infrared light source 11.

System 10 may provide a rapid method of gas sensing and identification over a continuum spectral region without a need of multiple discrete sources to cover such spectral region and provide virtually all of the benefits of photoacoustic gas detection.

Photoacoustic spectroscopy may provide a highly sensitive approach for detecting very small concentrations of gases with a microphone at ppb (part-per-billion) levels, or with cantilever-interferometric pressure sensing at ppt (part-per-trillion) levels.

System 10 may be based primarily on the coupling of a Fourier transform infrared (FTIR) spectrometer illumination source 11 with a photoacoustic (PA) gas sensor or chamber 16. The Fourier transform (FT) spectrometer portion may generate a modulated infrared beam 12 which is coupled into the PA sensor measurement chamber 16. Each spectral wavelength of the output 12 of source 11 may be modulated at a frequency proportional to its wavelength and be dependent on how fast the FT spectrometer is scanned or modulated. If a gas of sample 19 absorbs this wavelength, then this absorption may generate a unique frequency of sound wave in the photoacoustic chamber 16 which is detected by the pressure sensing mechanism 22 (e.g., microphone, cantilever-interferometer, or the like) coupled to the chamber. There may be different detected sounds for different absorption peaks. For example, for a 3.3 micron peak, there may be a 10 Hz sound wave, and for a 4.3 micron peak, there may be a 7.7 Hz sound wave.

Processing the spectral content of the pressure sensing mechanism's 22 output signal may allow one to obtain the absorption spectral signatures or fingerprints of the gases present in the sample 19 within the photoacoustic measurement chamber 16.

Figure 2:
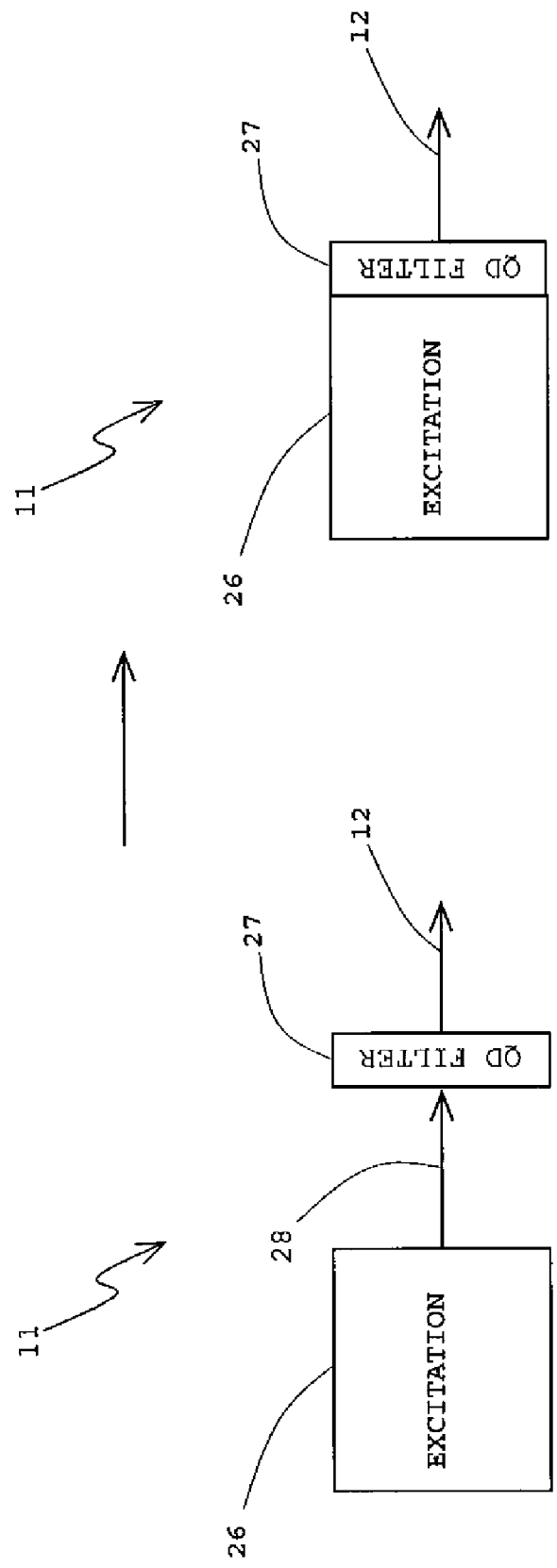
FIG. 2 is a diagram of a light source and its components.

System 10 may use source 11 which can be tailored for whatever spectral waveband one would like to cover. In FIG. 2, source 11 may be based on an excitation light portion 26, for example, a simple LED pumping a quantum dot (QD) filter 27 with light 28. By selection of the appropriate characteristic QD's, the desired spectral range of light 12 may be obtained with high efficiency generation with the pumping from an LED. This may allow for the obtaining of a highly efficient low powered IR source 11 covering the spectral range of interest.

In particular, the energy or light source 11 may produce radiant energy or light 12 which is modulated at a known frequency movement 15 with a lamellar grating 13. The modulated energy or light 12 may be provided to a cell or chamber 16 containing a gas sample 19 that absorbs the light 12 leading to temperature fluctuations in the gas that track the modulation frequency. Temperature is not sensed directly. Rather, pressure fluctuations that accompany the temperature fluctuations may be detected by pressure sensor 22 such as a sensitive microphone situated in chamber 16. The microphone output may be detected at a modulation or other frequency for obtaining an electrical signal indicative of gas identification and/or concentration.

Gas sensors based on the absorption of photons by a gas of interest, such as the photoacoustic sensing approach, generally need a modulatable infrared (IR) radiation source 11 that emits at the absorption band of the gas to be detected.

Figure 3:
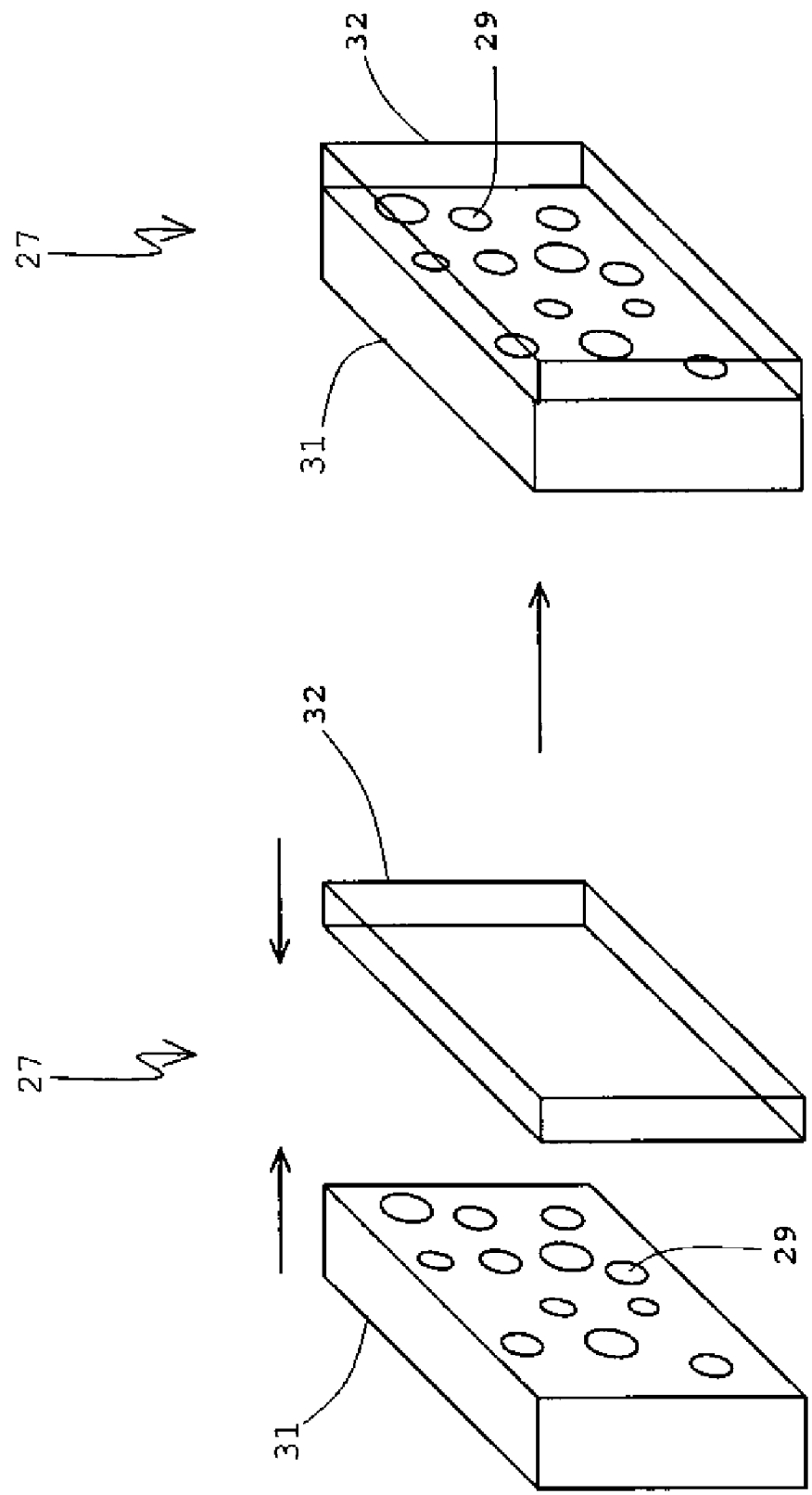
FIG. 3 is a diagram of an example quantum dot filter and its components.

Light 12 from source 11, based on the fluorescence of quantum dots 29 (FIG. 3) of a filter 27 in source 11, may allow modulation of light 12 to kHz levels and higher and might not require an optical interference filter. Higher light 12 modulation frequencies may yield a better signal to noise ratio and reduced sensitivity to background noise. The modulation of light 12 may be provided by lamellar grating 13. A modulation frequency of the grating may be at hundreds to thousands of hertz.

The power required for a quantum dot source 11 is potentially lower than that for an incandescent source producing comparable radiation in the waveband of interest. Additionally, a quantum dot source 11 may produce longer wavelengths of IR radiation at a significantly lower cost than is currently possible with other approaches, thereby allowing a low-cost portable photoacoustic sensor 10 to be produced.

A quantum dot filter 27, located proximate to an LED, or other source of excitation 26, may emit a specific wavelength of light 12 to be received by the chamber 16. The excitation component 26 and filter 27 may constitute light source 11, as shown in FIG. 2. A LED, for instance, may provide excitation light of about 470 nanometers. The specific wavelength emitted by the present quantum dot source 11 may be between 1 and 4.3 microns, with a possible option of extending further into the infrared. Other designs of source 11 may provide light having a wavelength range from less than one micron out to at least sixteen microns. Such range may be sufficient for obtaining a signature or fingerprint of many different fluids.

Excitation light portion 26 of light source 11 may generate a light 28 spectrum. Excitation portion 26 may be selected based on several characteristics including cost and power consumption. The excitation portion 26 may be an LED, an array of LEDs, an LED pump, a laser, a laser diode, or other suitable device.

A light 12 spectrum may be generated by source 11. The spectrum of light 12 may be selected according to the design and sensitivity of quantum dot filter 27 of source 11. Quantum dots 29 may generally absorb light at a shorter wavelength than the wavelength at which they emit light via fluorescence. Therefore, a light 28 spectrum may be selected so as to obtain a desired wavelength, such as IR, of light emission from quantum dot filter 27. The light 28 spectrum may be within the spectrum of visible light, but need not be. For instance, the light 28 spectrum may include white light or ultraviolet (UV) light. Quantum dot filter 27 of FIG. 3 may consist of at least one layer of quantum dots 29 arranged two-dimensionally on an optically transparent substrate 31. Alternatively, dots 29 may be embedded and arranged two- or three-dimensionally in substrate 31. Quantum dots 29 may emit light via fluorescence. A photon from excitation light 28 may be absorbed by the quantum dots 29 and result in an electron-hole pair. The electron may be generated at a relatively high energy state and then relax back to the valance band. When this occurs, the electron and hole may recombine and emit a photon having a specific wavelength as light 12. The overall process may convert a photon from light 28 of one wavelength into a lower energy photon having another wavelength. The specific wavelength of the emitted photon may be dictated in part by the band gap of the quantum dot 29 material, and be essentially monochromatic for a given quantum dot diameter and material composition.

The quantum dots 29 may include lead selenide (PbSe), lead sulfide (PbS), mercury telluride (HgTe), or another suitable material, or any combination thereof. Dots 29 may be nano crystals. Quantum dots 29 may be of various shapes, although circular or spherical shapes might be common. Quantum dots 29 may have various sizes, although sizes from single digit to double digit nanometers might be common. The quantum dot substrate 31 may be formed by any suitable manner. Quantum dot filter 27 may be formed by direct printing of quantum dots 29 in a random pattern. The quantum dot filter may be formed by direct printing of quantum dots in an arranged structure. Arrangements of quantum dots 29 may be made in view of size, shape, material, intra-dot one-, two- and/or three-dimensional spatial relationships, and so on. If desired, a protective layer 32 may be added over the quantum dots to protect them from the environment. The present quantum dot filter 27 may have a coating of quantum dots 29 applied to a glass substrate 31 and coated with a protective layer 32. Quantum dots 29 may be mixed in with a substance designed to be a filter or window. For instance, quantum dots 29 may be mixed in with a plastic (e.g., quantum dot doped plastic) which may be used as a light exit window of an LED or the like.

The quantum dot filter 27 may fluoresce within a narrow band when subjected to the light 28 spectrum and thus emit light 12 of a specific wavelength. The width of the spectral band of the quantum dot filter 27 may be tuned through careful selection and use of quantum dots 29. The quantum dot substrate 31 may include quantum dots 29 of a uniform material composition and size to produce a monochromatic IR source, or may include quantum dots of varying size and/or composition to produce a source 11 having a complex IR emission spectrum. For example, if it is desirable for quantum dot filter 27 to fluoresce across a wide band of wavelengths, quantum dots 29 of varying sizes may be used to assemble a quantum dot substrate 31. Similarly, if it is desirable for quantum dot filter 27 to fluoresce across an extremely narrow band, quantum dots 29 having virtually identical sizes and the same material may be used. An array of interchangeable quantum dot substrates 31 may be used, each emitting a suitable predetermined but different specific wavelength, wavelength band, or spectrum.

The specific wavelength emitted by quantum dot light source 11 may depend generally on the size and composition of the quantum dots on substrate 31, and may be selected according to the particular gas 19 that the photoacoustic cell or chamber 16 is to detect. The term specific wavelength may refer to a wavelength of the peak intensity of the energy emitted by a quantum dot source 11. The specific wavelength may be tuned by controlling the geometry of quantum dots 29. In general, depending on the material, smaller quantum dots 29 may fluoresce at lower wavelengths (into the visible), whereas larger quantum dots 29 may fluoresce in the red and infrared region. For example, a quantum dot substrate 31 assembled from relatively small quantum dots may emit a specific wavelength that is shorter, has higher energy, and is therefore bluer, than a quantum dot substrate assembled from relatively large quantum dots, which may emit a longer, and therefore redder, specific wavelength. The quantum dot substrate 31 may have quantum dots ranging in size from, for example, approximately two to sixty nanometers.

The specific wavelength may be chosen to broadly coincide with the strongest absorption band of the gas 19 to be detected by photoacoustic chamber 16. Typically, the specific wavelength may be in the infrared (IR) band. For instance, if photoacoustic chamber 16 is to be used to detect generic hydrocarbons, the specific wavelength may be chosen to fall within the range of approximately 3.0-3.5 microns. Alternatively, a source 11 design may be such that the specific wavelength of light 12 emitted by quantum dot light source 11 is in the range of one to four microns. As another alternative, a design of source 11 may be such that the specific wavelength of light 12 emitted by quantum dot light source 11 is in the range of three to four microns. Such source 11 of system 10 may be designed to detect, for example, generic hydrocarbons, methane ($CH_4$), or sulfur dioxide ($SO_2$). For example, a specific wavelength of light 12 emitted by the quantum dot source 11, being approximately 3.3 microns, may be used for detecting methane. Another wavelength of light 12, being approximately four microns, may be used for calibrating photoacoustic chamber 16.

Chamber 16 may serve as a measurement volume for system 10. Chamber 16 may be generally cube, cylindrical, or like shaped, and may have a volume of approximately one cubic centimeter.

Pressure sensor 22, such as a microphone, may be sensitive to acoustic signals, and be positioned to detect pressure changes within chamber 16. Pressure changes within chamber 16 may be caused by gases absorbing the radiant energy of a specific wavelength and changing temperature as a result. The temperature fluctuations in the gas may track the modulation frequency of specific wavelength. Within chamber 16, pressure fluctuations that accompany the temperature fluctuations may be detected by pressure sensor 22. Any suitable acoustic transducer, such as the microphone, may be used as sensor 22. For example, the microphone may be an electret microphone. As another example, the microphone may be one having piezoelectric material.

An outer wall of chamber 16 may be constructed of any suitable material. The outer wall may include a metal, such as aluminum. In an alternative, the outer wall may include a plastic, or polymer, such as methacrylate.

A gas permeable wall 21 of chamber 16 may be a porous membrane formed of paper, a porous metal, or a gas permeable polymer. Thus, after the photoacoustic chamber 16 is located for several minutes within a given environment, the gas mixture within chamber may substantially match the gas mixture of the surrounding environment.

Figure 5:
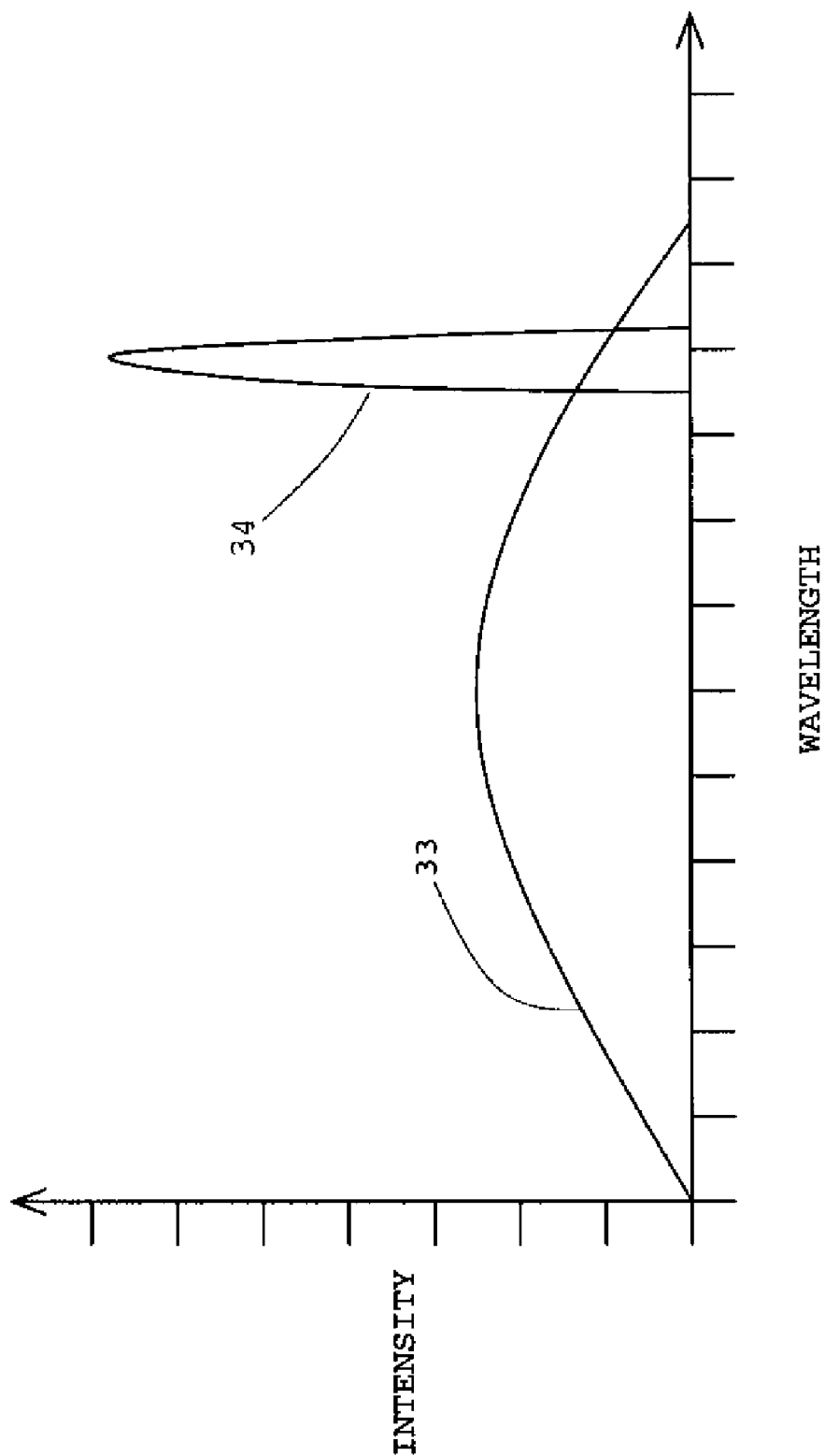
FIG. 5 is a graph of examples of broad band and narrow band light.

FIG. 5 is a diagram of a graph shows how the light spectrum 33 generated by light source 11 may cover a broad range of wavelengths (shown on the x-axis, in microns). The graph also shows that the specific wavelength 34 emitted by source 11 may be within a narrow range of wavelengths in the IR band, and have a significantly longer wavelength than the wide light spectrum 33.

Figure 4:
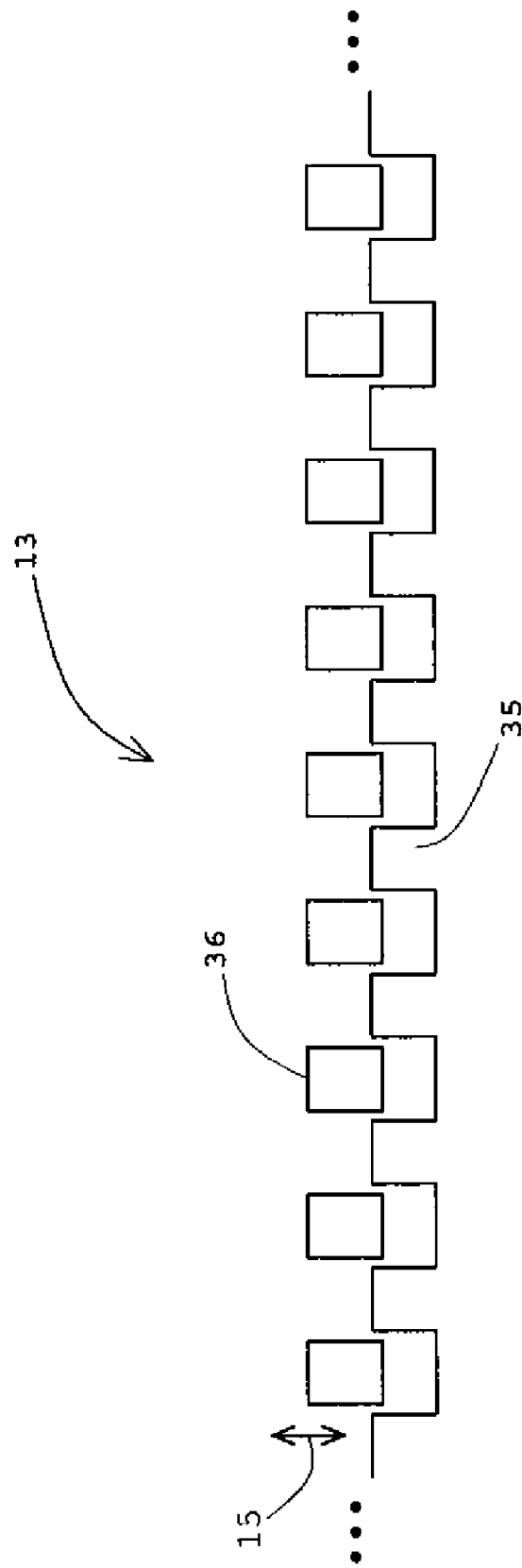
FIG. 4 is a diagram of a lamellar grating.

The lamellar grating based FTIR spectrometer 10 may be a simple form of a FTIR spectrometer requiring no beamsplitter. The lamellar grating 13 of FIG. 4 may be a binary grating having a variable depth, which operates in the zero order of the diffraction pattern. Grating 13 may be like a beamsplitter having two surfaces, like that of a mirror, but one moveable and one fixed. Grating 13 may have an overall concave shape for a focused reflection of light 12 ultimately from source 13 to chamber 16 via the intermediate reflection devices 14 and 17, respectively. A lens situated in front of a planar lamellar grating may also be used. The lamellar grating 13 interferometer may divide the wavefront into two wavefronts at a grating where the front facets 35 (a set of fixed mirrors) reflect one half of the beam, and the back facets 36 (a set of mobile mirrors with movement 15) reflect one half of the beam. One layout of the sets of mirrors may be like interleaved fingers. The distance between the front mirrors 35 and back mirrors 36 may determine the optical path difference (OPD) between the two wavefronts. Grating 13 may incorporate a MEMS comb drive. The acoustic modulation frequency in the photoacoustic cavity for a given radiation wavelength may be equal to $2V/\lambda$, where V is a velocity of the moving mirror of the lamellar grating 13 and $\lambda$ is the wavelength of the light 12.

The lamellar grating FTIR spectrometer 10 may reduce part count and provide a compact form factor for gas spectroscopy. MEMS may be used to produce the lamellar grating 13 and photoacoustic chamber 16 for system 10.

System 10 may have a temperature sensor 41, another pressure sensor 42, and a photodiode 43. Temperature sensor 41 may be coupled to pressure sensor 22. Temperature sensor 41 may measure the temperature of pressure sensor 22 in order to generate a correction signal to compensate for temperature induced changes in sensitivity of pressure sensor or mechanism 22. Any suitable temperature measurement device may be used. An example of temperature sensor 41 may include a thermocouple.

Pressure sensor 42 may be situated at chamber 16. Pressure sensor 42 may measure the atmospheric pressure about chamber 16 in order to generate a pressure correction signal. Pressure sensor 42 may be used to compensate for variations in the environment surrounding photoacoustic chamber 16. For example, pressure sensor 42, may be used to compensate for changes in barometric pressure caused by a change in altitude or weather conditions. Any suitable pressure measurement mechanism may be used.

Photodiode 43 may be to measure the intensity of the light 12 emitted by light source 11. Photodiode 43 may be used to monitor the intensity of light 12 for purposes of calibrating photoacoustic gas sensing system 10.

Processor 23 may receive signals related to pressure changes in chamber 16. Processor 23 may be electrically connected to light source 11. Processor 23 may include circuitry for controlling light source 11, as well as circuitry for receiving and processing signals from pressure sensor 22, temperature sensor 41, pressure sensor 42, and photodiode 43. Processor 23 may perform calculations on the signals to identify the one or more gases within chamber 16 and a concentration corresponding to each of those gases. The signals from temperature sensor 41, pressure sensor 42 and photodiode 43 to processor 23 may be used for calibrating photoacoustic chamber 16 and compensating pressure sensor 22. Modulation driver 44 signals may also be accounted for by processor 23. Processor 23 may be any type of computational circuit, such as, but not limited to, a microprocessor, a microcontroller, or a computer.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications

What is claimed is:

1. A spectroscopy system comprising:
a light source;
a lamellar grating coupled to the light source;
a photoacoustic chamber coupled to the grating; and
a pressure sensor coupled to the chamber.

2. The system of claim 1, wherein the grating is for modulating light from the light source to the photoacoustic chamber.

3. The system of claim 2, wherein the pressure sensor is for detecting pressure changes in the photoacoustic chamber which reveal information about contents in the chamber.

4. The system of claim 3, wherein the pressure changes are caused by absorption elicited from the contents in the chamber by the light.

5. The system of claim 3, wherein the light source is a quantum dot light source.

6. The system of claim 5, wherein the light source is for providing light having a wavelength range between one and five microns.

7. The system of claim 5, wherein the light source has a wavelength range between one and sixteen microns.

8. The system of claim 5, wherein the light source comprises:
an excitation device having a light output; and
a quantum dot filter coupled to the light output of the excitation device.

9. The system of claim 8, wherein the excitation device is an LED, laser diode.

10. A method for spectroscopy comprising:
providing light;
modulating the light with a lamellar grating;
conveying the light from the grating to a photoacoustic chamber; and
detecting pressure changes within the photoacoustic chamber.

11. The method of claim 10, wherein:
the light is provided from a quantum dot light source.

12. The method of claim 11, wherein:
the quantum dot light source comprises:
an excitation device; and
a quantum dot conversion filter coupled to the excitation device; and
the conversion filter is designable to provide a certain bandwidth of light from the quantum dot light source.

13. The method of claim 12, wherein the bandwidth of light is sufficient to elicit one or more absorption lines from a sample of one or more gases, respectively, in the photoacoustic chamber and cause pressure changes in the chamber that reveal information about the one or more gases.

14. A photoacoustic spectroscopy system comprising:
a light source;
a modulatable lamellar grating coupled to an output of the light source;
a photoacoustic chamber coupled to an output of the grating; and
a pressure sensor situated in the chamber.

15. The system of claim 14, wherein:
the light source is a quantum dot source.

16. The system of claim 14, wherein:
the light source comprises:
an excitation device; and
a quantum dot conversion filter coupled to the excitation device; and
a bandwidth of the light source is customizable according to a design of the quantum dots in the filter.

17. The system of claim 15, wherein:
the lamellar grating is a MEMS device; and
the photoacoustic chamber is a MEMS device.

18. The system of claim 14, wherein:
the pressure sensor is for detecting pressure changes in the photoacoustic chamber which reveal information about contents in the chamber; and
the pressure changes are caused by absorption lines elicited from the contents in the chamber by the light.

19. The system of claim 14, further comprising:
a temperature sensor for detecting temperature in the photoacoustic chamber;
a second pressure sensor for detecting ambient pressure about the chamber; and/or
a photodiode for measuring intensity of the light from the light source; and
wherein outputs from the temperature sensor, the second pressure sensor and/or the photodiode are used for calibrating the photoacoustic chamber and/or for compensating signals about a sample in the chamber from the pressure sensor situated in the chamber.

* * * * *